(12) United States Patent
Rademacher et al.

(10) Patent No.: US 6,900,182 B1
(45) Date of Patent: May 31, 2005

(54) INOSITOLPHOSPHOGLYCAN AND RIBOSE FOR TREATMENT OF ISCHAEMIA-REPERFUSION INJURY

(75) Inventors: Thomas William Rademacher, Oxford (GB); Leslie Greenbaum, Surrey (GB); Patricia McLean, Surrey (GB)

(73) Assignee: Sylus Pharmaceuticals Ltd., London (GB)

( * ) Notice: Subject to any disclaimer, the term of this patent is extended or adjusted under 35 U.S.C. 154(b) by 0 days.

(21) Appl. No.: 09/719,909

(22) PCT Filed: May 12, 1999

(86) PCT No.: PCT/GB99/01499

§ 371 (c)(1),
(2), (4) Date: Mar. 1, 2001

(87) PCT Pub. No.: WO00/00205

PCT Pub. Date: Jan. 6, 2000

(30) Foreign Application Priority Data

Jun. 29, 1998 (GB) .............................................. 9814039

(51) Int. Cl.$^7$ .................... A61K 31/70; A61K 31/7028; A61K 31/7076; C07H 15/00
(52) U.S. Cl. ............................. 514/25; 514/23; 514/42; 514/45; 514/46; 514/35; 536/4.1; 536/18.7; 536/17.2; 536/109
(58) Field of Search ............................. 514/25, 23, 42, 514/45, 46, 35; 536/4.1, 18.7, 17.2, 109, 18.4

(56) References Cited

U.S. PATENT DOCUMENTS 4,880,783 A * 11/1989 Mentzer et al. ................ 514/46

FOREIGN PATENT DOCUMENTS

WO     WO 9811435 A1 *  3/1998  .......... G01N/33/53

OTHER PUBLICATIONS

Pliml et al.(Clinical investigator, (Oct. 1993) 71 (10) 770–3) (Abstract sent).*
Asplin et al., P.N.A.S. 90:5924–5928, 1993.
Berne, Amer. J. Physio., 204:317–322, 1963.
Bouchard and Lamontagne, Cardiovasc. Res., 37:82–90, 1998.
Bromme and Holz, Mol. Cell Biochem. 163–164:261–275, 1996.
Bozkurt et al., Cardiovasc. Surg., 5; 117–124, 1997.
Caro et al., Biochem. Molec. Med., 61:214–228, 1997.
Choong and Gavin, J. Cardiovasc. Surg. (Torino), 37:275–284, 1996.
de Jong et al., Eur. J. Pharmacol., 337:41–44, 1997.
Ferrari et al., Cardiovasc. Drugs Ther., 10:425–437, 1996.
Gilad et al., . Mol. Cell Cardiol., 29:2585–2597, 1997.
Hillier et al., Amer. J. Epidemiol., 128:402–409, 1988.
Houston et al., J. Cell Mol. Cardiol., 29:1763–1766, 1997.
Jaramillo et al., J. Org. Chem., 59:3135–3141, 1994.
Konorev et al., Br. J. Pharmacol., 199:511–518, 1986.
Kunjara et al., Biochem J., 244:101–108, 1987.
Loh et al., Br. J. Pharmacol., 118:1905–1012, 1996.
Mangano, J. Amer. Med. Assoc., 277:325–332, 1997.
Meldrum et al., Immunology 92:472–477, 1997.
Muhlhauser et al., Diabetologia, 40:1492–1493, 1997.
Pernow & Wang, Cardiovasc. Res., 33:518–526, 1997.
Rademacher et al., Brazilian J. Med. Biol. Res., 27:327–341, 1994.
Russ et al., Pflügers Arch., 433:26–34, 1996.
Smits & Their, Diabetologia 38:116–212, 1995.
Stanley et al., Cardiovasc. Res., 33:243–257, 1997.
Thiemermann et al., P.N.A.S. (USA), 94:679–683, 1997.
Varela–Nieto et al., Comp. Biochem. Physiol., 115:223–241, 1998.
Zapata et al., Carbohydrate Res., 264:21–31, 1994.
Zimmer, J. Physiol. (Paris), 76:769–775, 1980.
Zimmer, Science, 220:81–82, 1983.
Zimmer, Mol. Cell Biochem., 160–161, 101–109, 1996.
Zingarelli et al., Shock, 5:258–264, 1996.
Zubairu et al., J. Neurochemistry, 41:76–83, 1983.
Danforth et al., Circ. Res., 7:965–870, 1983.
Goodwin et al., Eur. J. Cardiothorac. Surg., 11:981–987.
Kunjara et al., In: Biopolymers and Bioproducts Structure, Function and Applications, Ed. Svati et al., 301–305, 1995.

* cited by examiner

Primary Examiner—James O. Wilson
Assistant Examiner—Michael C. Henry
(74) Attorney, Agent, or Firm—Jonathan Alan Quine; Quine Intellectual Property Law Group, P.C.

(57) ABSTRACT

Compositions comprising inositolphosphoglycans (IPGs) and ribose are disclosed, and their use in the prevention or treatment of ischaemic-reperfusion injury. This treatment increases the energy generating systems of cells by employing the mitochondrial oxidative restoration system. The use of the compositions in preserving organs for transplantation is also disclosed.

7 Claims, 8 Drawing Sheets

PRPP CONTENT OF LIVER

CONTROL FED RAT LIVER = 100%

Fig. 4 (A) Lipogenesis. Adipocyte assay.
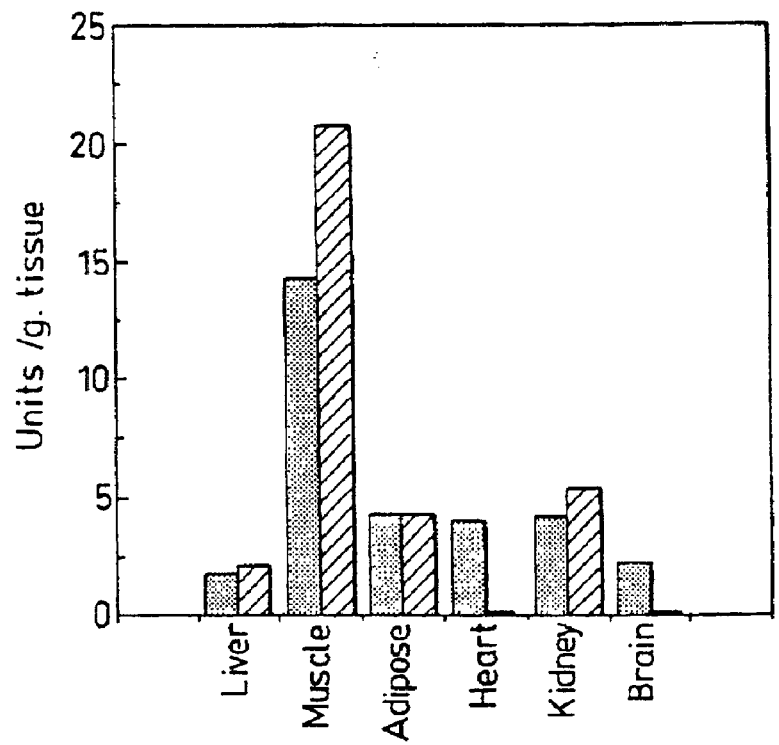
Fig. 4 (B) cAMP-dependent protein kinase-A assay
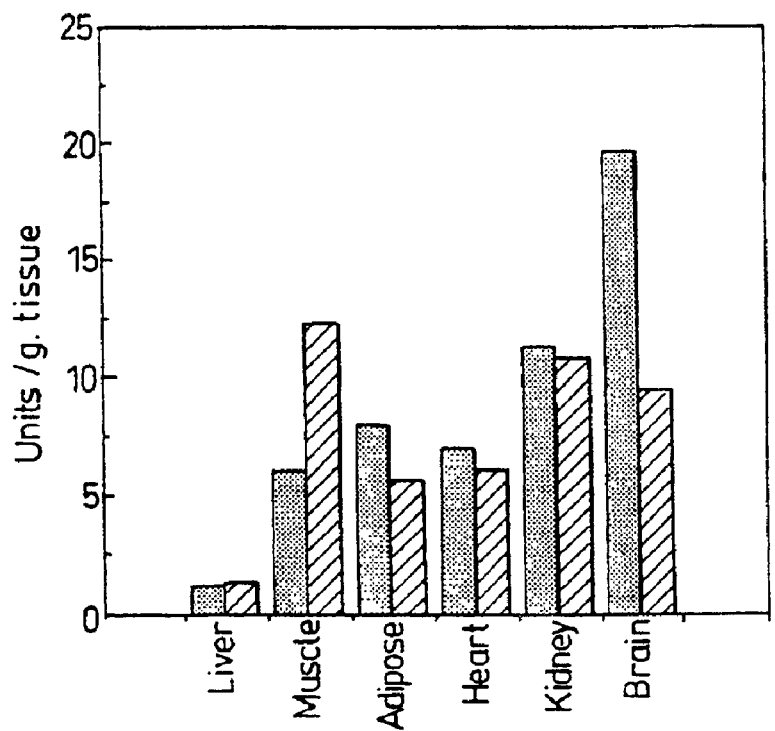

Fig. 4 (C) PDH phosphatase assay
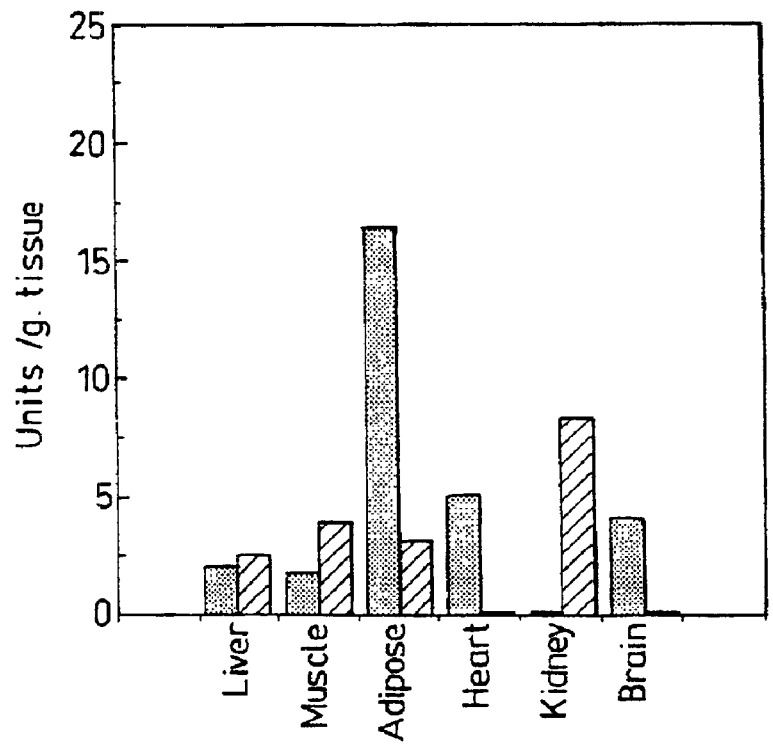
Fig. 4 (D) cAMP-dependent protein kinase-P assay
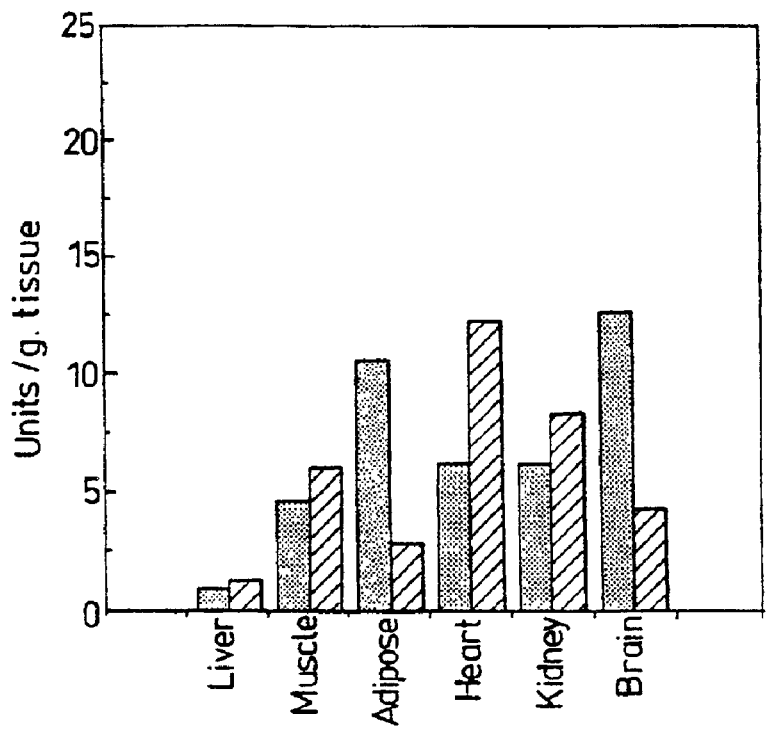

INOSITOLPHOSPHOGLYCAN AND RIBOSE FOR TREATMENT OF ISCHAEMIA-REPERFUSION INJURY

FIELD OF THE INVENTION

The present invention relates to material and methods relating to the prevention or treatment of ischaemia-reperfusion injury, and in particular to compositions comprising inositolphosphoglycans (IPGS) and their medical use in the prevention or treatment of ischaemia.

BACKGROUND OF THE INVENTION

The search for novel therapies for ischaemic-reperfusion injury in the heart has been a subject of intense research, both for recovery from open-heart surgery, where the limited capacity for the heart to survive ischaemia is a well researched problem (Stanley et al, 1997), and from the viewpoint of modulating the extent of damage incurred during episodes of cardiac ischaemia (Stanley et al, 1997). It is also well established that the incidence of coronary heart disease is a major factor in the morbidity and mortality of diabetic patients (Fuller et al, 1983; Hillier et al, 1988). There is also evidence that standard drugs for the treatment of diabetes of the sulphonylurea group may have negative effects, including those on $K^+$ channel function (smits & Thien, 1995; Muhlhauser et al, 1997).

The complexity of the events following ischaemia-reperfusion is such that there is a very wide ranging database of potential therapeutic and cardioplegic agents targeting differing aspects of the cascade leading to damage to cardiac function. It has been apparent from work as early as the 1960s (Danforth et al, 1960; Berne, 1963) to the present (Zimmer, 1996; Houston et al, 1997) that a key feature of the cascade of interlinked biochemical events following ischaemic-reperfusion injury centres on the loss of adenine nucleotides from the myocardium. There is, thus, an absolute requirement for the restitution of the intracellular ATP concentration and the energy charge of the cell in order to restore normal cardiac function.

Adenine nucleotide synthesis can occur via utilization or reutilisation of adenine nucleotide breakdown products via the salvage pathway, or via de novo synthesis from small molecular weight precursors. The former is the most effective in terms of energy requirement (Mangano, 1997; Meldrum et al, 1997).

However, in addition to the requirement for the purine ring, a supply of phosphoribosylpyrophosphate (PRPP) is essential both for the salvage and de novo routes of synthesis; this latter compound is, in turn, subject to tight regulation and is dependent upon a supply of ribose-5-phosphate (Kunjara et al, 1987). Zimmer (1980) demonstrated that restitution of myocardial adenine nucleotides was accelerated by ribose, as was the normalisation of depressed heart function in rats (Zimmer, 1983). This author stated that "The advantage of ribose over other metabolic interventions is that is does not affect the haemodynamics of the heart with an ultimate change in oxygen demand and that is has no vasoactive properties which may result in afterload alterations".

Recently, Zimmer (1996) reported that in two in vivo rat models, the overloaded and catecholamine-stimulated heart and the infarcted heart, the normalisation of the cardiac adenine nucleotide pool by ribose was accompanied by improvement in global heart function. Further, the combined treatment with ribose and adenine or inosine in isoproteronal-treated rats was more effective in the restoration and completely restored the ATP level within a shorter period of time than either treatment alone.

SUMMARY OF THE INVENTION

While the results showing the effect of repletion of cardiac ATP are encouraging, the prior art approaches described above suffer from the disadvantage that the biosynthetic pathways themselves require ATP, as does the reconversion of AMP to ADP and ATP, the required ATP being the very compound in short supply. Further, as mentioned above, the complexity of the biochemistry associated with ischaemia means that it is not clear from the prior art how alternative approaches could avoid this problem.

The present invention relates to the finding that inositolphosphoglycans (IPGs), and in particular P-type IPGs, or their synthetic analogues, can be used to generate ATP from ADP while helping to avoid the production of toxic byproducts and helping to minimise the ATP requirement for the process. Thus, compositions comprising IPGs can be used to prevent or treat ischaemia-reperfusion, in particular in conditions where there is a reduction or risk of reduction in cellular ATP levels, e.g. in cardiac ischaemia, in surgery (especially heart or transplant surgery), in preserving organs for transplantation, in the treatment of stroke and as an anti-apoptosis agent to protect against cell death (especially in muscle cells).

Accordingly, in a first aspect, the present invention provides a composition for treating an ischaemic-reperfusion injury, the composition comprising an inositolphosphoglycan (IPG) or an IPG synthetic analogue, and ribose.

In a further aspect, the present invention provides the use of an inositolphosphoglycan (IPG) for the preparation of a medicament for the treatment of ischaemic-reperfusion injury.

The IPGs present in the medicament can be P- or A-type IPGs, or synthetic analogues of them. The production of IPGs and IPG analogues is discussed further below. Preferably, the IPG is a P-type IPG or a P-type synthetic analogue.

The present invention is based on the realisation that an alternative approach to the problem of increasing the energy generating systems of the cell is to employ the mitochondrial oxidative restoration system, in particular by the regulation of the key enzyme for the entry of pyruvate into the tricarboxylic acid cycle, pyruvate dehydrogenase. Accordingly, the present proposal centres upon the use of naturally occurring activators of pyruvate dehydrogenase phosphatase, the inositolphosphoglycans, to promote the conversion of pyruvate dehydrogenase to the active form, thereby enhancing the rephosphorylation of AMP and ADP.

Advantageously, the composition includes one or more other components, in combination with the IPGs, for use in the treatment of ischaemia-reperfusion injury as described herein. Among the agents to be used in combination with IPGs from different sources are:

(1) Adenosine and purine compounds as precursors of ATP and as modulators of TNFα action (see Bouchard & Lamontagne, 1998; de Jong et al, 1997; Meldrum et al, 1997).

(2) Ribose as a precursor of PRPP (see Kunjara et al, 1987; Zimmer, 1996).

(3) Nicotinamide and derivatives to prevent the loss of NAD and ATP by inhibition of poly-ADP ribose synthetase (see Bromme & Holz, 1996; Zingarelli et al, 1996; Gilad et al, 1997; Thiememann et al, 1997).

(4) ca$^{2+}$uptake inhibitors (see Ferrari et al, 1996; Loh et al, 1998; Russ et al, 1996).

(5) Addition of IPGs to established cardioplegic solutions (see Choong and Gavin, 1996; Bozkurt et al, 1997).

(6) Maintenance of glutathione systems (see Konorev et al, 1996). Glutathione in its reduced form (GSH) is an important factor in the prevention of damage by hydrogen peroxide. Hydrogen peroxide is a component of ischaemia-reperfusion injury and protection is afforded by the action of glutathione peroxidase and GSH. The importance of GSH and the pentose phosphate pathway in the chain reactions protecting the cell from free radical damage is illustrated in FIG. 1 from Zubairu et al, 1983.

(7) Endothelin inhibitors (see Goodwin et al, 1997; Pernow & Wang, 1997). Endothelin-1 (ET-1) is an extremely potent vasoconstrictor peptide derived from vascular endothelial cells. During and following myocardial ischaemia and reperfusion, the myocardial production and release of ET-1 is stimulated and the coronary constriction to ET-1 is enhanced. The pathophysiological role for ET-1 in the development of ischaemia has a strong basis and the potential for cardioprotective effects of ET-1 antagonists has been considered by Pernow and Wang (1997).

Ischaemia-reperfusion injury can arise in a wide range of conditions and the medicament can be used to treat these conditions. Examples include ischaemia resulting from myocardial infarct, during surgery (especially open heart surgery, or during organ transplantation, e.g. employing the medicament as a cardioplegia solution for heart or lung bypass surgery), and in stroke. The medicament can also be used to ameliorate the effects of ischaemia in tissues, in particular as an anti-apoptotic agent to prevent cell death following ischaemia, e.g. muscle cell death.

In a further aspect, the present invention provides a method for preserving an organ for transplantation, the method comprising exposing the organ with a composition comprising an inositolphosphoglycan (IPG), and optionally one or more of the components mentioned above. As ischaemia is common in organs for transplantation, this approach is useful for preserving the energy level present in the organ prior to transplantation and during surgery. Conveniently, the composition can be perfused through the organ or used to store the organ prior to transplantation, i.e. be a storage medium for the organ.

In a further aspect, the present invention provides compositions comprising a P-type IPG and ribose. In these compositions, the IPG drives mitochondrial oxidation and results in ATP generation from ADP without production of toxic byproducts. Preferably, the composition additionally comprises a purine or purine nucleotide precursor to provide the basic structural element of ATP. Other possible components of the composition are described above.

This composition is useful in organ preservation, in general surgery (e.g. as a perfusion fluid) and in other situations for the prevention or treatment of ischaemia in cells. Preferably, the composition is supplied as a powder or concentrate from which a liquid composition can be prepared. Alternatively, the composition can be supplied ready to use in as a liquid. Formulations and optional ingredients of the composition are discussed further below.

In further aspects, the present invention provides above compositions for use in a method of medical treatment, for example in the preparation of a medicament for the treatment of ischaemic conditions discussed above.

Embodiments of the present invention will now be described by way of example and not by limitation with reference to the accompanying drawings.

BRIEF DESCRIPTION OF THE DRAWINGS

FIG. 4A shows the results of a lipogenesis assay and FIG. 4B shows a CAMP-dependent protein kinase A assay. The solid columns show results in the absence of insulin, while the hatched columns show results 2 minutes after injection with insulin. 1 unit is the amount of A-type IPG causing a 50% increase in the basal rate of lipogenesis or a 50% decrease in the activity of cAMP dependent protein kinase.

FIG. 4C shows a PDH phosphatase assay and FIG. 4D shows a cAMP-dependent protein kinase-P assay. The solid columns show results in the absence of insulin, while the hatched columns show results 2 minutes after injection with insulin. 1 unit is the amount of P-type IPG causing a 50% increase in the activity of PDH phosphatase or a 50% decrease in the activity of cAMP dependent protein kinase.

DETAILED DESCRIPTION OF THE INVENTION

IPGs and IPG Analogues

Figure 1:
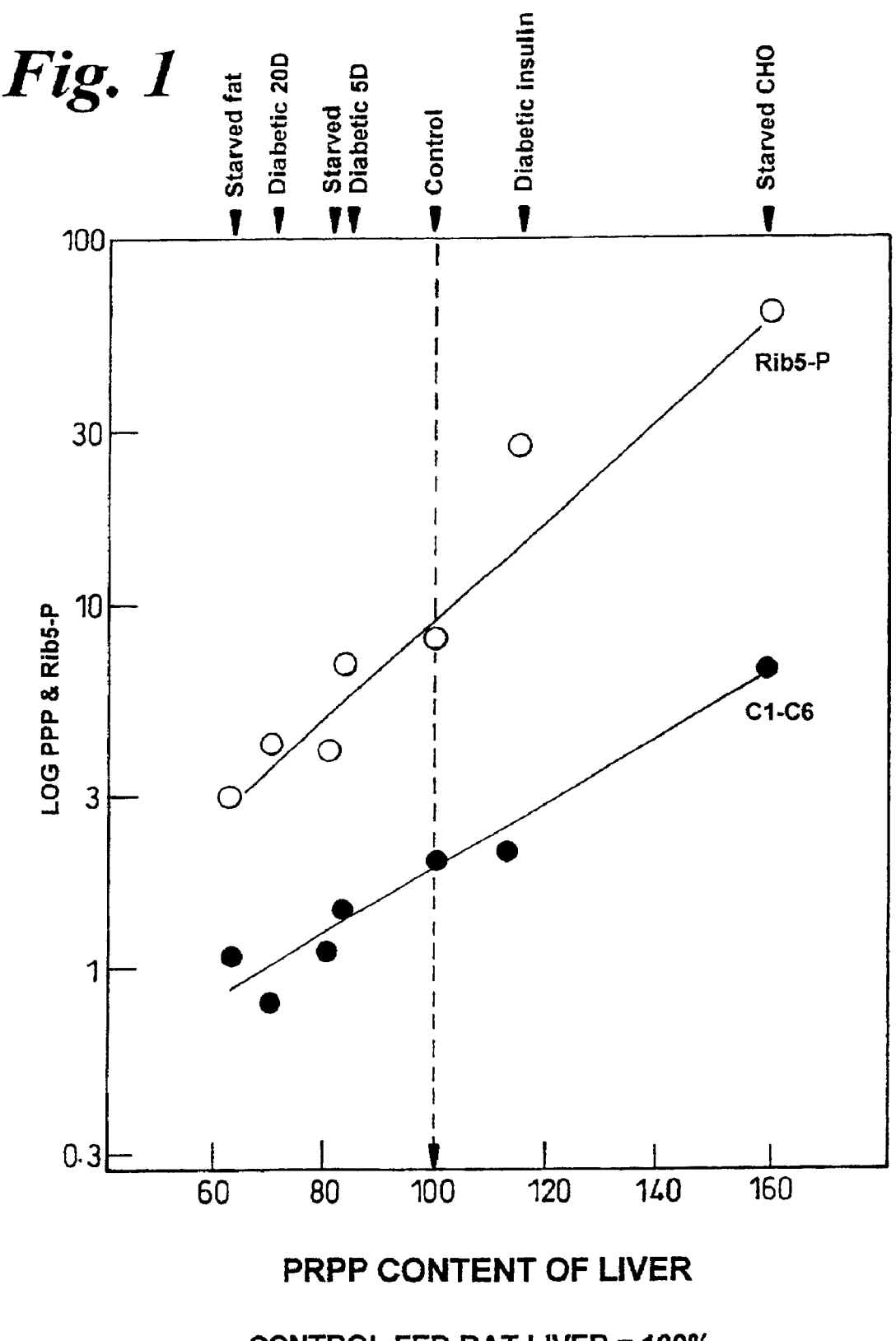
FIG. 1 shows the correlation between the hepatic PRPP concentration and the log of ribose 5-phosphate and the flux through the oxidative pentose phosphate assay pathway (C1–C6) in different dietary and hormonal conditions in rats.

Studies have shown that A-type mediators modulate the activity of a number of insulin-dependent enzymes such as cAMP dependent protein kinase (inhibits), adenylate cyclase (inhibits) and cAMP phospho-diesterases (stimulates). In contrast, P-type mediators modulate the activity of insulin-dependent enzymes such as pyruvate dehydrogenase phosphatase (stimulates), glycogen synthase phosphatase (stimulates) and cAMP dependent kinase (inhibits). The A-type mediators mimic the lipogenic activity of insulin on adipocytes, whereas the P-type mediators mimic the glycogenic activity of insulin on muscle. Both A-and P-type mediators are mitogenic when added to fibroblasts in serum free media. The ability of the mediators to stimulate fibroblast proliferation is enhanced if the cells are transfected with the EGF-receptor. A-type mediators can stimulate cell proliferation in the chick cochleovestibular ganglia.

Soluble IPG fractions having A-type and P-type activity have been obtained from a variety of animal tissues including rat tissues (liver, kidney, muscle brain, adipose, heart) and bovine liver. A- and P-type IPG biological activity has also been detected in human liver and placenta, malaria parasitized RBC and mycobacteria. The ability of an anti-inositolglycan antibody to inhibit insulin action on human placental cytotrophoblasts and BC3H1 myocytes or bovine-derived IPG action on rat diaphragm and chick cochleovestibular ganglia suggests cross-species conservation of many structural-features. However, it is important to note that although the prior art includes these reports of A- and P-type IPG activity in some biological fractions, the purification or characterisation of the agents responsible for the activity is not disclosed.

A-type substances are cyclitol-containing carbohydrates, also containing $Zn^{2+}$ ion and optionally phosphate and having the properties of regulating lipogenic activity and inhibiting CAMP dependent protein kinase. They may also inhibit adenylate cyclase, be mitogenic when added to EGF-transfected fibroblasts in serum free medium, and stimulate lipogenesis in adipocytes.

P-type substances are cyclitol-containing carbohydrates, also containing $M^{2+}$ and/or $Zn^{2+}$ ions and optionally phosphate and having the properties of regulating glycogen metabolism and activating pyruvate dehydrogenase phosphatase. They may also stimulate the activity of glycogen synthase phosphatase, be mitogenic when added to fibroblasts in serum free medium, and stimulate pyruvate dehydrogenase phosphatase.

Methods for obtaining A-type and P-type IPGs are set out in Caro et al, 1997 and in WO98/11116 or WO98/11117. The present invention can employ IPGs found in nature, for instance in tissues such a liver or placenta from animals such as human, pig, rat or other animals), and obtained using methods described in the above applications. These IPGs are preferably purified from the tissues, and more preferably purified to homogeneity. As defined herein, "substantially purified" describes IPGs which have been separated from components which are naturally present with the IPGs in the source tissue. Preferably, the compositions are at least 75%, more preferably at least 90%, more preferably at least 95%, and still more preferably at least 99% by weight of IPGs.

Alternatively or additionally, the present invention can employ cyclitol-containing IPG analogues, e.g. inositol-containing IPG analogues. These compounds have the advantage that they can be more readily prepared using synthetic organic chemistry methods, rather than being extracted from natural source materials. Preferred P-type synthetic analogues contain chiro-inositol, or a derivative thereof, as a structural unit or motif, and have one or more of the properties of P-type IPGs indicated above, especially activation of pyruvate dehydrogenase phosphatase. An example of a chiro-inositol containing IPG analogue is compound C4, 1D-6-O-(2-amino-2-deoxy-α-D-glucopyranosyl)-chiro-inositol 1-phosphate which can be synthesised as described in Jaramillo et al, 1994.

Preferred A-type synthetic analogues contain myo-inositol, or a derivative thereof, as a structural unit or motif and have one or more of the properties of A-type IPGs indicated above. An example of a myo-inositol containing IPG analogue is compound C3 1D-6-O-(2-amino-2-deoxy-α-D-glucopyranosyl)-myo-inositol 1,2-(cyclic phosphate), which can be been prepared as described in Zapata et al, 1994.

Pharmaceutical Compositions

The compositions of the invention can be formulated according to the specific application which the composition is intended to treat. The compositions may comprise, in addition to the one or more IPGs, and optionally one or more of the above components, a pharmaceutically acceptable excipient, carrier, buffer, stabiliser or other materials well known to those skilled in the art. Such materials should be non-toxic and should not interfere with the efficacy of the active ingredient(s). The precise nature of the carrier or other material may depend on the route of administration, e.g. intravenous, cutaneous or subcutaneous, nasal, intramuscular, intraperitoneal routes. For embodiments in which the medicaments or compositions of the invention are used in organ preservation, they can be formulated so that they are suitable for storing or perfusing organs or tissue.

The compositions may be supplied in the form of a powder or concentrate from which a composition can be prepared. Alternatively, the composition may be supplied in a ready to use form, e.g. as a liquid. In either event, the composition may include other active ingredients, adjuvants or carriers. Thus, physiological saline solution, dextrose or other saccharide solution or glycols such as ethylene glycol, propylene glycol or polyethylene glycol may be included.

In embodiments in which the composition is used in the prophylactic or therapeutic treatment of conditions associated with a risk of ischaemia, preferably the composition is administered to a patient via intravenous, cutaneous or subcutaneous injection, or injection at the site of affliction. In this case, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as sodium chloride injection, Ringer's injection, lactated Ringer's injection. Preservatives, stabilisers, buffers, antioxidants and/or other additives may be included, as required. Injection is a preferred mode of delivery for compositions for treating ischaemia that results from myocardial infarction, stroke or to treat or protect against apoptosis.

The active ingredients in the composition are preferable administered to an individual in preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in *Remington's Pharmaceutical Sciences*, 16th edition, Oslo, A. (ed), 1980.

A composition may be administered alone or in combination with other treatments, either simultaneously or sequentially dependent upon the condition to be treated.

Experimental

Experiments in this laboratory have shown with rat heart preparations that the tissue PRPP concentration in anoxic conditions fell and was partially restored by addition of ribose to the medium. Perhaps of greater significance was our observation of the decline in cellular PRPP in a range of tissues, including heart, in experimental diabetes (see Table 1). These data suggest that ribose or a ribose precursor and/or purine derivatives could advantageously be included in the medicaments compositions of the invention.

While reported effects of repletion of cardiac ATP are encouraging, it is apparent that these biosynthetic processes themselves require ATP, as does the reconversion of AMP to ADP and ATP, the required ATP being the very compound in short supply. Thus, any mechanism increasing the energy generating systems of the cell, primarily and most effectively via the mitochondrial oxidative restoration, would be advantageous to the process of cellular restoration. In this context, the regulation of the key enzyme for the entry of pyruvate into the tricarboxylic acid cycle, the pyruvate dehydrogenase complex, must be considered.

This enzyme is highly regulated by, among other factors, the energy status of the cell, by the NADH/NAD+ ratio and by the acetyl COA/CoA ratio, via the interconversion of active/inactive forms of pyruvate dehydrogenase by phosphorylation/dephosphorylation reactions regulated by pyruvate dehydrogenase kinase and regulation of this enzyme complex at the pyruvate crossroads. This system operates in a manner such that ischaemic conditions activate PDH kinase dehydrogenase and so shut off energy production at this step. In order to circumvent this inhibition, even in ischaemia, it is necessary to activate the PDH phosphatase and this can be accomplished by the presence of IPGs. Pyruvate dehydrogenase activity is the most important determinant of whether pyruvate is converted to lactate, leading to lactic acidosis and a low level of ATP from glycolysis, or whether the highly efficient ATP generating system of the tricarboxylic acid cycle will be facilitated.

The present invention centres upon the use of naturally occurring activators of pyruvate dehydrogenase phosphatase, the inositolphosphoglycans, to promote the conversion of pyruvate dehydrogenase to the active form (Rademacher et al, 1994; Varela-Nieto et al, 1998), thereby enhancing the rephosphorylation of AMP and ADP. The preferred combination of purine nucleotide precursors (to provide the basic structural element of the required ATP), together with ribose (to provide the ribose 5-phosphate for PRPP formation) and inositolphosphoglycans (to shift the pyruvate dehydrogenase complex towards the active form, generate energy and decrease lactic acidosis) can be used to treat ischaemic conditions, e.g. ischaemic heart conditions, and the loss of ATP. As can be seen from FIG. 5, such a therapy would supply all three major elements required for the restoration of the energy charge of the cell.

(1) Ribose, as the precursor of the synthesis of the adenine lost from the cell during extended ischaemia;
(2) PRPP, an essential component of the adenine biosynthetic pathway; and,
(3) An increase energy yield from carbohydrate fuel which can provide the energy needed for biosynthetic processes in (1) and (2) and also to rephosphorylate such ADP and AMP as remains in the cell to ATP.

Therefore, the approach of using inositolphosphoglycans either alone or together with other precursors of adenine nucleotide synthesis and compounds protecting against loss of ATP (e.g. by inhibition of poly ADP ribose), in the treatment of ischaemic conditions in heart, kidney, brain or other organs, is a fundamental new approach to attempting to limit cell damage. In a preferred embodiment of the invention, the combination of ribose, purine precursors and nicotinamide, the latter to prevent lost of NAD and ATP by inhibition of polyADP ribose synthase, with the inositolphosphoglycans, the potent second messenger system functioning in the regulation of protein phosphorylation/dephosphorylation cycles, is a multifaceted attack on the very basis of cellular damage in ischaemic conditions, that is the loss of ATP.

Figure 5:
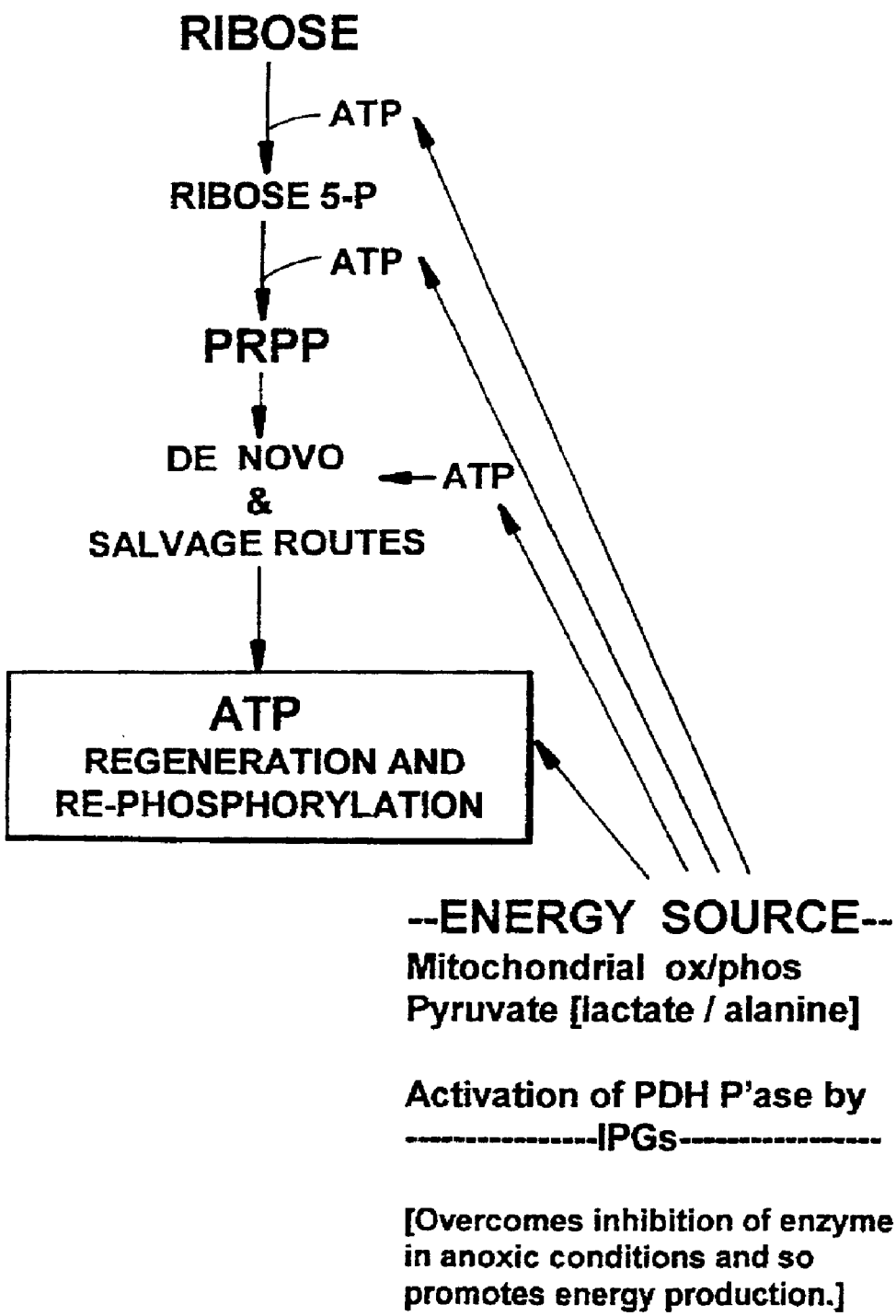
FIG. 5 shows a schematic setting out the role of ribose, IPGs and selected substrates on the prevention or recovery from ischaemic damage according to the present invention.

Table 1 demonstrates that in diabetes, there is a drop in tissue levels of PRPP. This drop could make diabetic patients more at risk of morbidity following an ischaemic attack. It is well established that both the incidence and complications of coronary heart disease are elevated in diabetic patients and decreased tissue levels of PRPP could be the crucial link. Thus, the present invention is particularly suited to the treatment of ischaemic conditions arising from diabetes. FIG. 1 demonstrates that tissue levels of ribose 5-phosphate are important in maintaining PRPP levels and FIG. 5 shows that ribose is the direct precursor of ribose 5-phosphate. Therefore, one important component in maintaining high levels of PRPP is to provide ribose as the precursor for ribose 5-phosphate.

Figure 2:
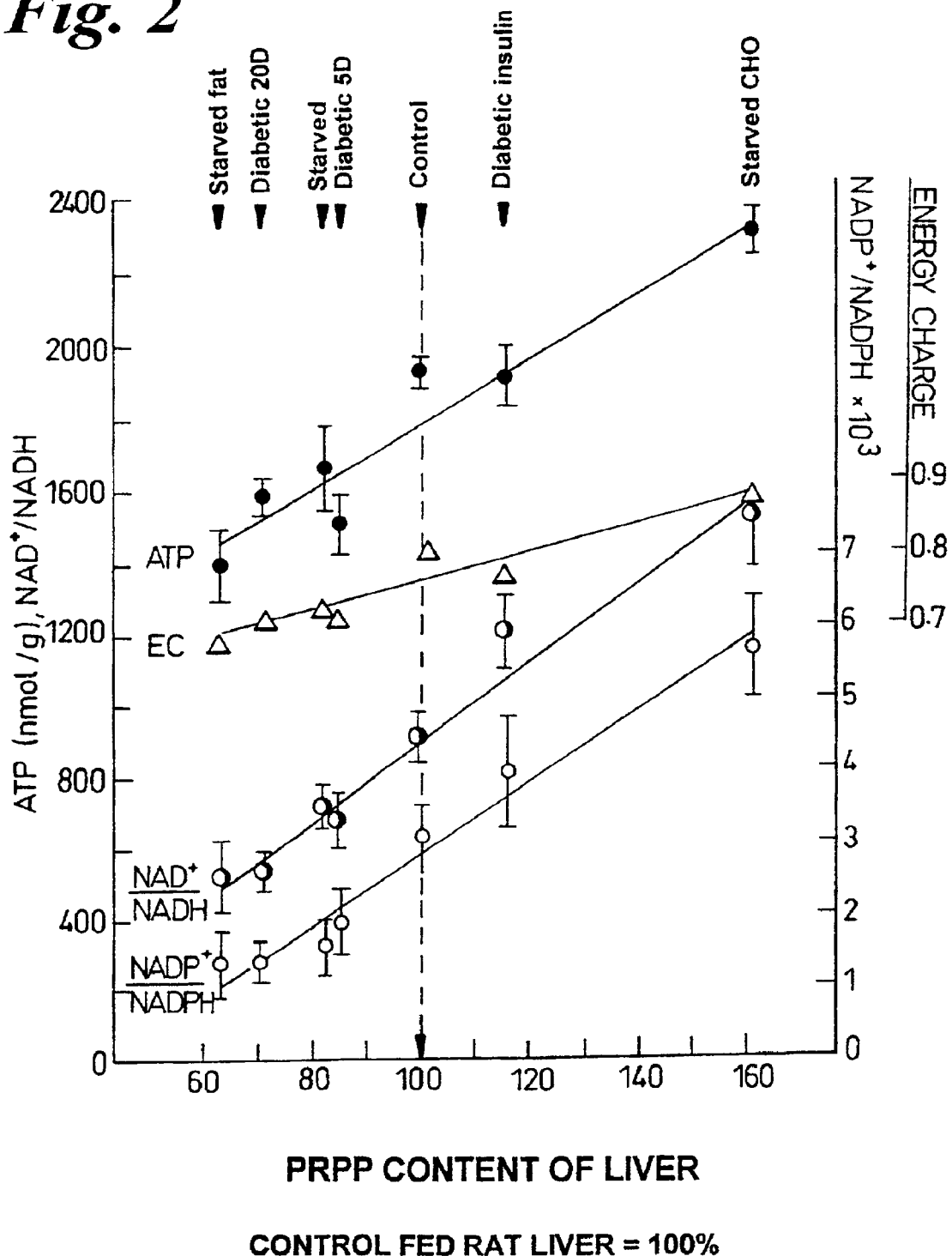
FIG. 2 shows the correlation between the hepatic PRPP concentration and ATP and energy charge (EC), free cytosolic NAD$^+$/NADH and NAD$^+$/NADPH in different dietary and hormonal conditions in rats.
Figure 3:
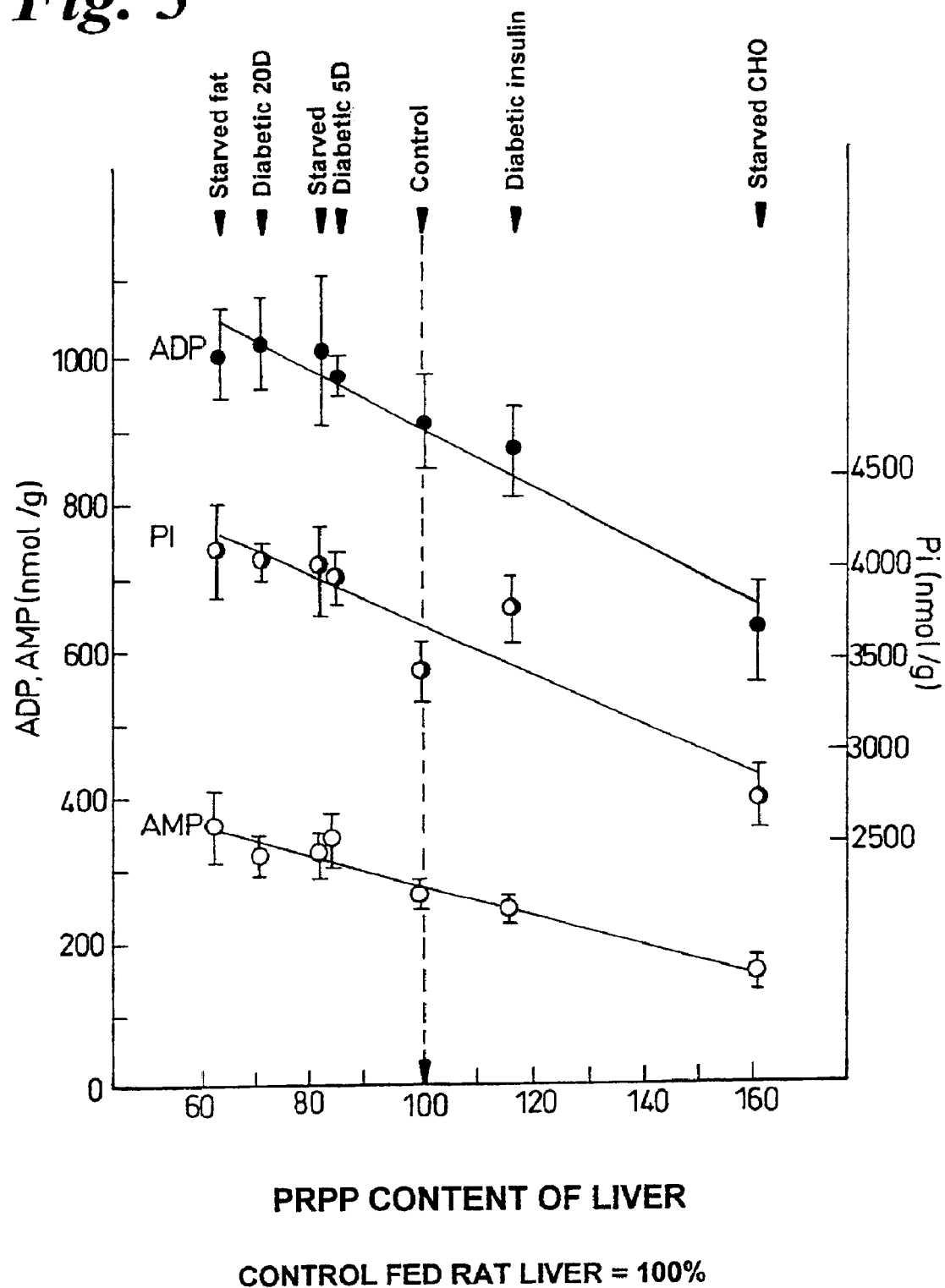
FIG. 3 shows the correlation between the hepatic PRPP concentration and ADP, AMP and Pi in different dietary and hormonal conditions in rats.
Figure 4:
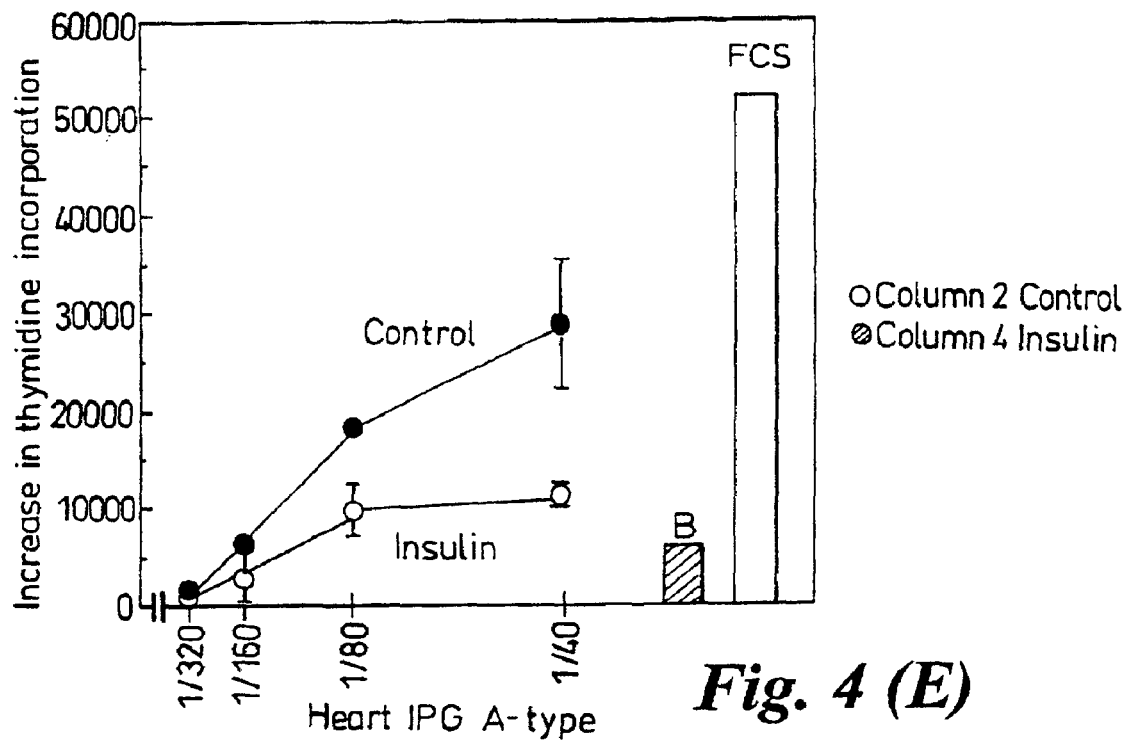
FIGS. 4A and 4B shows the steady state concentration and the effect of insulin on extractable IPG A-type from the heart and other tissues from adult male rats.
FIGS. 4C and 4D show the steady state concentration and the effect of insulin on extractable IPG P-type from heart and other tissues from adult male rats.
FIGS. 4E and 4F show the results of a thymidine incorporation into EGF receptor transfected 3T3 cells, plotted against IPG A-type and IPG P-type concentrations respectively.
Figure 4:
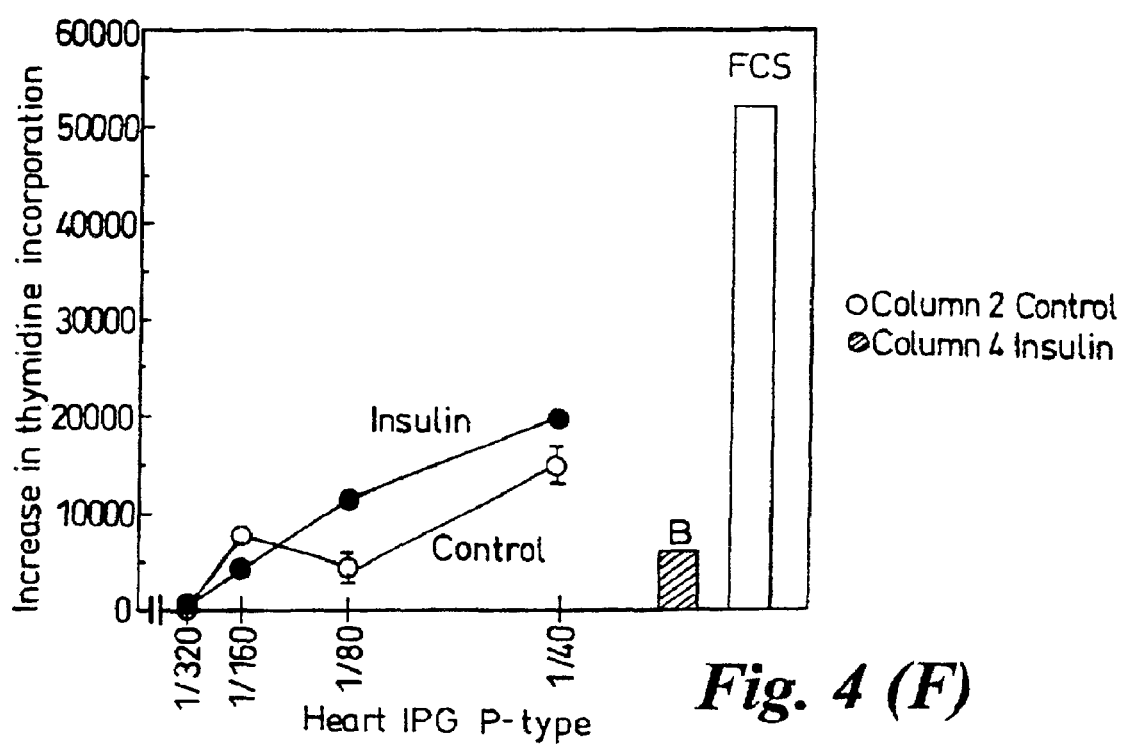
Figure 6:
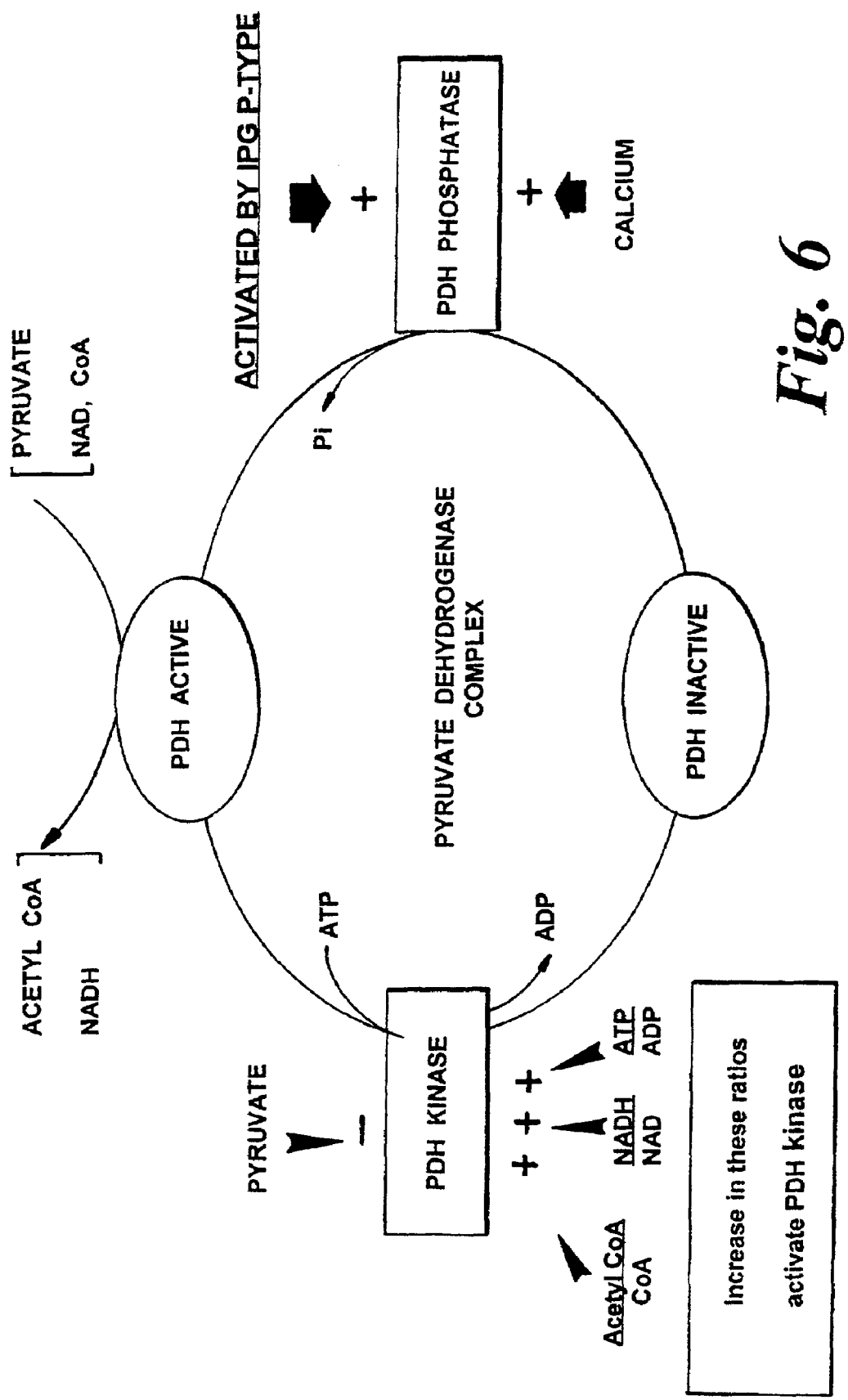
FIG. 6 shows a schematic setting out the site of action of IPG P-type in the activation of the PDH complex.

FIGS. 2 and 3 demonstrate that in order to have high levels of PRPP in tissues, the cellular energy charge must be high. Under anoxic conditions, this is difficultsince the enzyme PDH kinase is activated. The action of this enzyme is to inactivate the PDH complex, which is involved in the biosynthesis of acetyl-CoA and NADH. The NADH so generated in the reperfusion period is oxidized by the electron transport chain to generate ATP. The acetyl-CoA is a substrate for the Krebs cycle in which one glucose can be oxidized to 36 ATPs via the generation of further NADH. The action of IPG-P type mediators is to activate PDH phosphatase which counteracts the PDH kinase and allows for activation of the PDH complex. This activation is shown in FIG. 6. The action of the IPG-P type and the amounts recovered from various tissues before and after insulin infusion are shown in FIGS. 4C and D. In particular, an increase in activity is found in muscle and kidney upon insulin infusion. In contrast, decreased activity is found in heart, adipose tissue and brain (FIG. 4C). These data demonstrate that an insulin infusion could not substitute for a direct infusion of the IPG-P type. FIG. 5 shows that an insulin infusion will also affect the IPG-A activity differentially in tissues and this effect would not occur on infusion of just IPG-P compound or its analogues.

TABLE 1

EFFECTS OF EXPERIMENTAL DIABETES ON PHOSPHORIBOSYL PYROPHOSPHATE (PRPP) CONTENT OF HEART AND OTHER TISSUES PHOSPHORIBOSYL PYROPHOSPHATE CONTENT (nmoles/g tissue)

| Tissue | Control | STZ Diabetic (14 Days) | "P" |
| --- | --- | --- | --- |
| Heart | 3.61 ± 0.11 (15) | 2.60 ± 0.20 (6) | <0.01 |
| Liver | 10.5 ± 0.64 (17) | 7.60 ± 0.43 (5) | <0.001 |
| Lung | 5.40 ± 0.05 (16) | 3.44 ± 0.39 (5) | <0.001 |
| Testis | 5.0 ± 0.30 (20) | 2.5 ± 0.9 (5) | <0.02 |
| Blood glucose (mM) | 7.0 ± 0.45 (25) | 28 ± 3.0 (7) | <0.001 |
| Body weight (g) | 309 ± 17 (20) | 226 ± 21 (7) | <0.01 |

The tissues were freeze-clamped and the PRPP content estimated as described by Kunjara et al (1987). The values are given as means±SEM; Fisher's P values are given. The adult male rats were used 14 days after the induction of diabetes with streptozotocin.

REFERENCES

The following references are cited to show the state of the art.

Asplin et al, P.N.A.S., 90:5924–5928, 1993.
Berne, Amer. J. Physiol., 204:317–322, 1963.
Bouchard & Lamontagne, Cardiovasc. Res., 37:82–90, 1998.

Bozkurt et al, Cardiovasc. Surg., 5;117–124, 1997.
Bromme & Holz, Mol. Cell Biochem., 163–164:261–275, 1996.
Caro et al, Biochem. Molec. Med., 61:214–228, 1997.
Choong & Gavin, J. Cardiovasc. Surg. (Torino), 37:275–84, 1996.
Danforth et al, Circ. Res., 7:965–870, 1983.
de Jong et al, Eur. J. Pharmacol., 337:41–44, 1997.
Ferrari et al, Cardiovasc. Drugs Ther., 10:425–437, 1996.
Gilad et al, J. Mol. Cell Cardiol., 29:2585–2597, 1997.
Goodwin et al, Eur. J. Cardiothorac. Surg., 11:981–987, 1997.
Hillier et al, Amer. J. Epidemiol., 128:402–409, 1988.
Houston et al, J. Cell Mol. Cardiol., 29:1763–6, 1997.
Jaramillo et al, J. Org. Chem., 59:3135–3141, 1994.
Konorev et al, Br. J. Pharmacol., 199:511–8, 1996;
Kunjara et al, Biochem. J., 244:101–108, 1987.
Kunjara et al, In: Biopolymers and Bioproducts: Structure, Function and Applications, Ed Svati et al, 301–305, 1995.
Loh et al, Br. J. Pharmacol., 118:1905–12, 1996.
Mangano, J. Amer. Med. Assoc., 277:325–332, 1997.
Meldrum et al, Immunology, 92:472–477, 1997.
Muhlhauser et al, Diabetologia, 40:1492–1493, 1997.
Pernow & Wang, Cardiovasc. Res., 33:518–526, 1997.
Rademacher et al, Brazilian J. Med. Biol. Res., 27:327–341, 1994.
Russ et al, Pflugers Arch., 433:26–34, 1996.
Smits & Their, Diabetologia, 38:116–121, 1995.
Stanley et al, Cardiovasc. Res., 33:243–257, 1997.
Thiemermann et al, P.N.A.S. (USA), 94:679–683, 1997.
Varela-Nieto et al, comp. Biochem. Physiol., 115:223–241, 1998
Zapata et al, Carbohydrate Res., 264;21–31, 1994.
Zimmer, J. Physiol. (Paris), 76:769–775, 1980.
Zimmer, Science, 220:81–82, 1983.
Zimmer, Mol. Cell Biochem., 160–161:101–109, 1996.
Zingarelli et al, Shock, 5:258–264, 1996.
Zubairu et al, J. Neurochemistry, 41:76–83, 1983.

What is claimed is:

1. A composition comprising an inositolphosphoglycan (IPG) or an IPG containing chiro-inositol or myo-inositol and ribose, wherein the IPG containing chiro-inositol or myo-inositol has the ability to activate pyruvate dehydrogenase phosphatase.

2. The composition of claim 1 wherein the IPG is a P-type IPG.

3. The composition of claim 1 wherein IPG containing chiro-inositol is a P-type IPG.

4. The composition of claim 1, further comprising adenosine or purine.

5. The composition of claim 1 or 2, wherein the composition is a liquid composition.

6. The composition of claim 1 or 2, wherein the composition is a powder or concentrate from which a liquid composition can be prepared.

7. The composition of claim 1 or 2, further comprising a pharmaceutically acceptable excipient.

* * * * *